United States Patent [19]

Visser

[11] Patent Number: 5,077,868
[45] Date of Patent: * Jan. 7, 1992

[54] DIAPER OR BABIES NAPKIN FASTENER

[75] Inventor: Hendrik S. Visser, East Lynne, South Africa

[73] Assignee: Snappi Holdings (Proprietary) Limited, Pretoria, South Africa

[*] Notice: The portion of the term of this patent subsequent to Oct. 16, 2007 has been disclaimed.

[21] Appl. No.: 509,330

[22] Filed: Apr. 13, 1990

Related U.S. Application Data

[60] Division of Ser. No. 359,987, Jun. 1, 1989, Pat. No. 4,962,571, which is a continuation-in-part of Ser. No. 228,295, Aug. 4, 1988, abandoned, which is a continuation-in-part of Ser. No. 184,285, Apr. 21, 1988, abandoned.

[30] Foreign Application Priority Data

Apr. 22, 1987 [ZA] South Africa ............... 87/2817

[51] Int. Cl.$^5$ .............................. A44B 1/04
[52] U.S. Cl. ................................. 24/301; 24/298; 24/265 H; 604/399
[58] Field of Search ........... 24/301, 72.5, 298, 300, 24/302, 370, 372, 230.5 R, 230.5 AD, 265 H; 604/386, 390, 399

[56] References Cited

U.S. PATENT DOCUMENTS 4,962,571 10/1990 Visser .................. 24/598.4 X

Primary Examiner—Laurie K. Cranmer
Attorney, Agent, or Firm—Christie, Parker & Hale

[57] ABSTRACT

A fastener for a baby's diaper is provided which comprises a generally elastic base member having at least thre claw units spaced apart thereon. The base member can be resiliently extended and the claw units engaged with a cloth or fabric diaper to retain the two ends of the part thereof encircling a baby's waist in required relative positions and also to hold a portion passing between the baby's legs in position relative to the former. The claw units are specially designed to properly engage the fabric of a diaper and not to become dislodged therefrom (if properly installed) in use. The fastener obviates the use of conventional safety pins with the associated disadvantages and dangers.

3 Claims, 3 Drawing Sheets

DIAPER OR BABIES NAPKIN FASTENER

RELATED APPLICATION

This is a Continuation of application Ser. No. 07/359,987, filed June 1, 1989, now U.S. Pat. No. 4,962,571, which is a Continuation-in-Part of application Ser. No. 07/228,295, now abandoned, Filed Aug. 4, 1988, which is a Continuation-in-Part of application Ser. No. 07/184,285, now abandoned, Filed Apr. 21, 1988.

FIELD OF THE INVENTION

This invention relates to a diaper or babies, napkin fastener particularly adapted for use in conjunction with a diaper (as a baby's napkin will herein be termed) which is made of cloth or woven fabric, as opposed to disposable paper products. The fastener of this invention is, however, not confined in application to such cloth or woven fabric diapers.

BACKGROUND TO THE INVENTION

Diapers can basically be divided into two categories, namely disposable diapers made predominantly of paper products, and which are generally fastened by means of fastening arrangements which include adhesive, in particular pressure sensitive adhesive, whereby two overlapping parts of a diaper can be secured together optionally by means of a strap, and a second category comprising cloth or woven fabric diapers, particularly those made of towelling material, and which are washable for re-use. The latter types of diaper are traditionally fastened using one or two safety pins to secure overlapping portions of the cloth or fabric together. The use of such safety pins is not only dangerous, both to the baby and person installing the safety pins in an operative position, but is also tedious.

It is the object of this invention to provide a fastener for use in conjunction with such cloth or fabric diapers which can more easily be rendered operative, and which may provide added comfort to a baby wearing a diaper fastened with such fastener and furthermore, which is also less dangerous or likely to cause injury either to the baby or person fitting the diaper.

SUMMARY OF THE INVENTION

In accordance with this invention there is provided a diaper fastener operative to hold a fabric diaper in position on a baby, the fastener comprising a flexible base member at least a part of which is elastically extensible, and at least three spaced relatively rigid claw units attached to the base member, the elastically extensible part of the base member being interposed between at least two of the claw units and wherein each claw unit has a body part which is substantially planar and has a free end region which extends transversely away from the body to terminate in a series of laterally spaced teeth offset from the plane of the body and directed inwardly towards a central region of the base member, the claw units being operative to engage the fabric of a diaper in relevant zones thereof with the elastically extensible part extended and being operative to maintain the teeth of the claw units in engagement with the fabric to hold the diaper in its functional position.

Further features of the invention provide for the base member to have a central zone from which three arms radiate, with a claw unit being attached to the end region of each arm opposite the central zone; for the central zone and arms to be integral with each other and to be made of flexible elastomeric material; for the entire base member to be made of injection moulded elastomeric plastics material; for each of the claw units to be defined by a separately manufactured and substantially rigid unit; and for such separately manufactured units to each have at least one headed formation passing through a hole in the associated region of the base member to retain the claw unit on the base member.

A still further feature of the invention provides for two of said arms to be arranged in substantially collinear relationship but extending in opposite directions from a central zone in which case the third arm extends outwardly at roughly right angles thereto.

A still further feature of the invention provides for a finger grip to be associated with each claw member; for each finger grip to be formed integral with the elastomeric material of the base member for the cross-sectional area of such finger grip to be appreciably less than the smallest cross-sectional area of the zone, generally an arm, which connects a claw unit with a central zone of the base member; and for the finger grip to be in the form of a ring.

Regarding the claw units, it is preferred that each claw unit has a minimum of three and preferably four or five teeth extending in a row across the width of the claw unit and that the free end region which extends transversely to the body part of each claw unit be either arcuate or inclined in side elevation.

It is to be noted that the material from which the base member is manufactured, as well as its cross-sectional dimensions, will dictate the force which need be used to extend the base member to render it operative. The force should not be too great and should not impose any undue stress on an infant in respect of which the fastener is used. It is for this reason that the cross-sectional dimensions of integral finger grips are preferably made less than the cross-sectional area of what will generally be arms connecting the claw units with a central zone of the base member so that extension of the finger grip will occur preferentially and a user will become aware of the fact that excessive stretching is being carried out.

It is to be noted that the offset between the series of teeth and the plane of the body part of each claw unit is extremely important as, with the teeth engaging in the fabric of a diaper, and the elastic force being exerted on the claw unit in a direction in which the teeth extend, will cause fabric of the diaper to gather in the space between the planar body part and the teeth which will ensure that the claw unit does not become disengaged from the fabric.

It is also to be noted that the length of the teeth is chosen such that the will be unable to penetrate more than about one layer of diaper fabric and, in general, they do not penetrate the fabric at all but rather hook into the fabric.

In order that the the invention may be more fully understood various embodiments thereof will now be described with reference to the accompanying drawings.

DETAILED DESCRIPTION WITH REFERENCE TO THE DRAWINGS

In the embodiment of the invention illustrated in FIGS. 1 to 5 of the drawings, a fastener, generally indicated by numeral is composed of a base member 2 made of injection moulded, soft, flexible, elastomeric plastics material.

Figure 1:
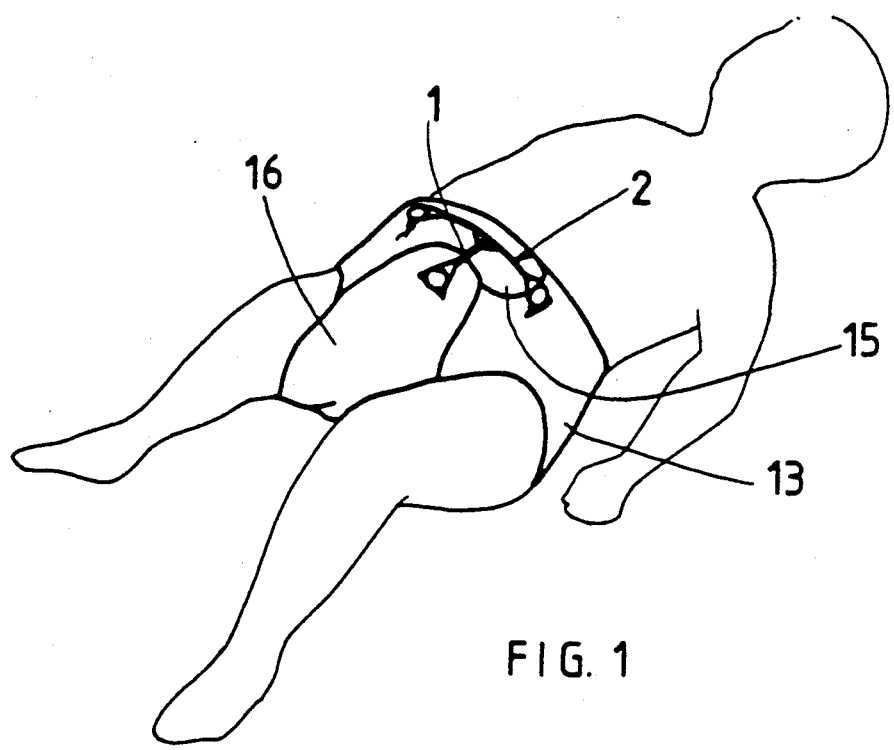
FIG. 1 is a perspective view illustrating a diaper on a baby and held in position by means of a fastener according to the invention.
Figure 2:
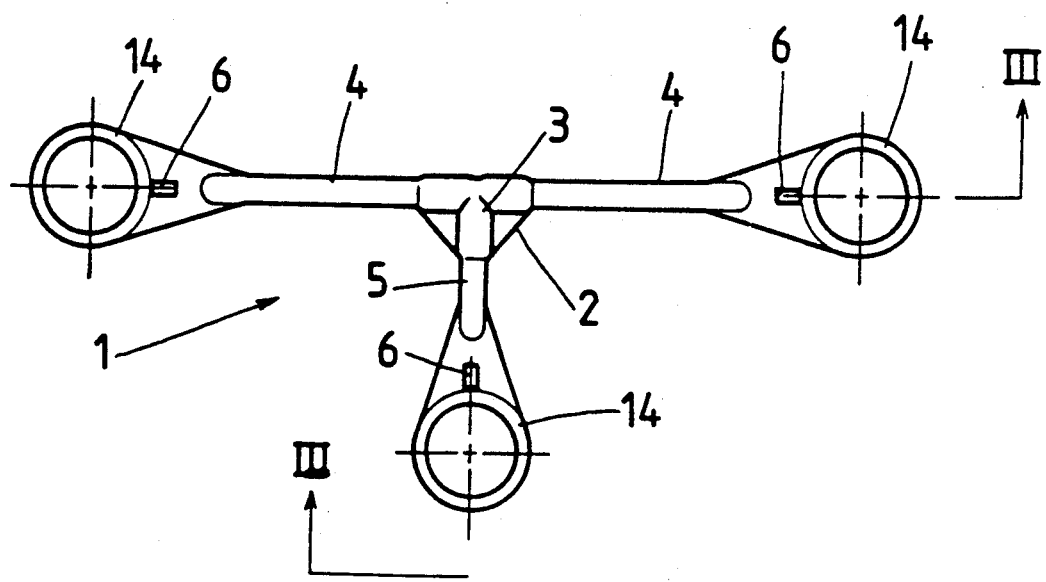
FIG. 2 is a plan view of a base member according to the invention without the claw units associated therewith.
Figure 3:
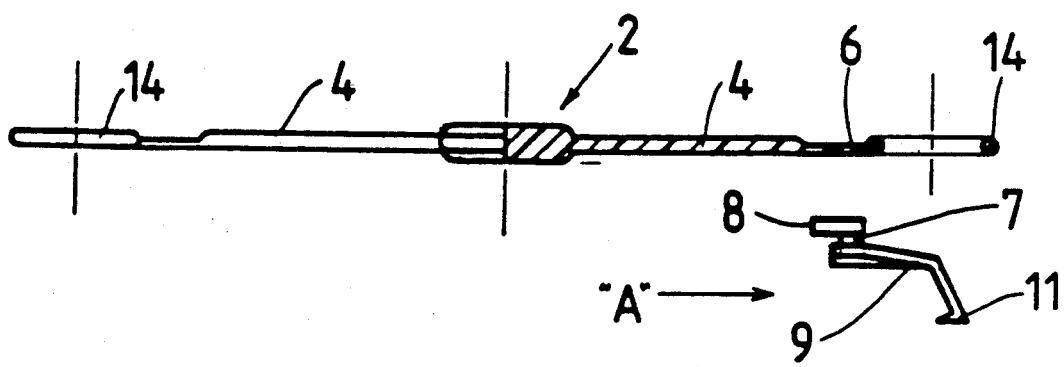
FIG. 3 is a partly sectioned elevation thereof illustrating one half of the base member in cross-section and one claw unit in exploded relationship relative thereto.
Figure 4:
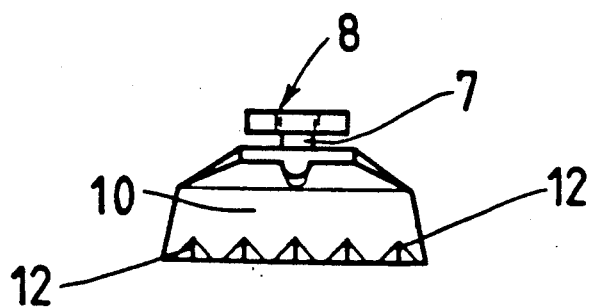
FIG. 4 is an end view of the claw unit of FIG. 3 taken in the direction of arrow "A" in FIG. 3.
Figure 5:
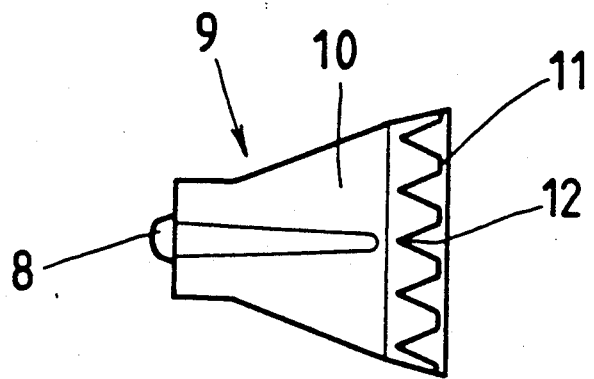
FIG. 5 is an inverted plan view of the claw unit illustrated in FIGS. 3 and 4; and, FIGS. 5, 7, & 8 each illustrate in plan view an alternative shape of the base member.

The base member, as shown most clearly in FIGS. 2 and 3, is moulded as one integral unit and comprises a central zone 3 from which radiate three arms, two longer ones 4 of which extend collinearly in diametrically opposite directions and a shorter one 5 of which extends at right angles thereto. Each of the arms is, accordingly, elastomerically extensible.

Towards the end of each arm is an elongated aperture 6 passing therethrough and adapted to accommodate the stem 7 of a headed formation 8 associated with a claw unit 9 injection moulded from relatively substantially rigid plastics material. The headed formation is, as shown in FIG. 3, located towards one end of the claw unit, the body part of which is substantially flat. Although only one such claw unit is illustrated in association with the base in FIG. 3, each of the arms carries one of such units.

Each of the claw units 9 extends, in the operative position, in the general direction of the arm with which it is associated and away from the central zone 3 and the free end region of the body part thereof passes through a transverse zone 10 (which may be arcuate or inclined) to terminate in a laterally offset free edge 11 defining a transverse series of inwardly directed spaced teeth 12. In this case there are five of such teeth spaced apart along the edge.

The direction in which the teeth 12 extend is slightly away from the plane of the base member but generally in a direction towards the central zone or towards the other claw units. These teeth are adapted to catch and engage in the fibres of a cloth or fabric diaper, as indicated by numeral 13 in FIG. 1 generally without passing through the diaper. The length of the teeth is therefore insufficient to pass through the fabric or at least through more than one layer thereof, and thereby injure or irritate a baby in use. In this case the length of the teeth is about 0.10 inches (2.6 mm) and their spacing about 0.14 inches (3.5 mm).

Moulded integral with each of the arms is a finger grip 14 which, in the operative position, lies above the associated claw unit 9. Such a finger grip not only assists in extension of the associated arm simply by pulling thereon but is also designed to give a user an indication as to the force to be applied to the associated arm when rendering it operative. This is achieved by making the cross-sectional area of the finger grip, which in this case is a simple ring shape, appreciably less than that of the associated arm. The feeling of adequate extension of the arm is thereby conveyed to the user by way of the finger grip. In general about 27 Newtons force has been found to be preferably applied to the arms during installation of the fastener.

In use, a baby's diaper 13, of the conventional towelling material for example, is passed around the torso of a baby and a central zone is passed upwardly between the legs in the usual manner.

The two overlapping portions 15 defining the ends of the portion of the diaper passing around the torso, each have one of the claw units engaged therewith in succession with the collinear arms 4 interconnecting same being extended suitably to provide a desired close fit of the diaper around the torso and extension being effected by means of the finger grips as indicated above.

The shorter arm 5 is then extended and its associated claw unit 9 engaged with the portion 16 of the diaper passing upwardly from between the legs of the baby.

It will be understood that the above described fastener will hold the diaper firmly in position and, due to its elasticity will indeed allow for movement and, it is considered, greater comfort to the baby. In this regard it has been found to be important that the series of teeth be laterally offset from the body of the claw unit as this provides space for the diaper fabric to become "bundled-up" in this space. This ensures that the teeth do not become disengaged from the fabric.

It will be seen that installation of the fastener provided by this invention is both swift and simple as well as being safe and not involving any danger to either the baby or the person installing the diaper in consequence of being pricked accidentally by a safety pin in all too well-known fashion.

Figure 6:
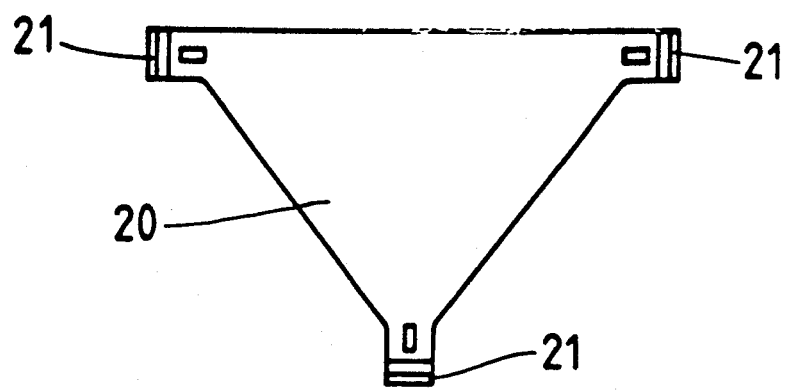
Figure 7:
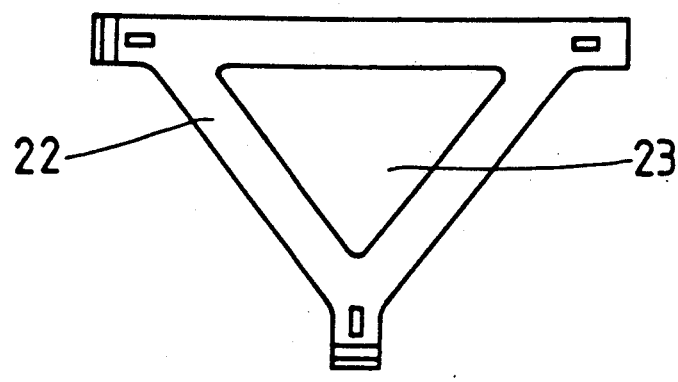

Various alternative shapes of the base member are also within the scope of this invention. Thus, as shown in FIG. 6, the base member 20 may be made of elastically extensible material but to a triangular shape with the hook or tooth formations 21 provided at the apices of the triangle. Alternatively, as shown in FIG. 7, the triangular shaped base member 22 may have the central zone removed as indicated by numeral 23.

Figure 8:
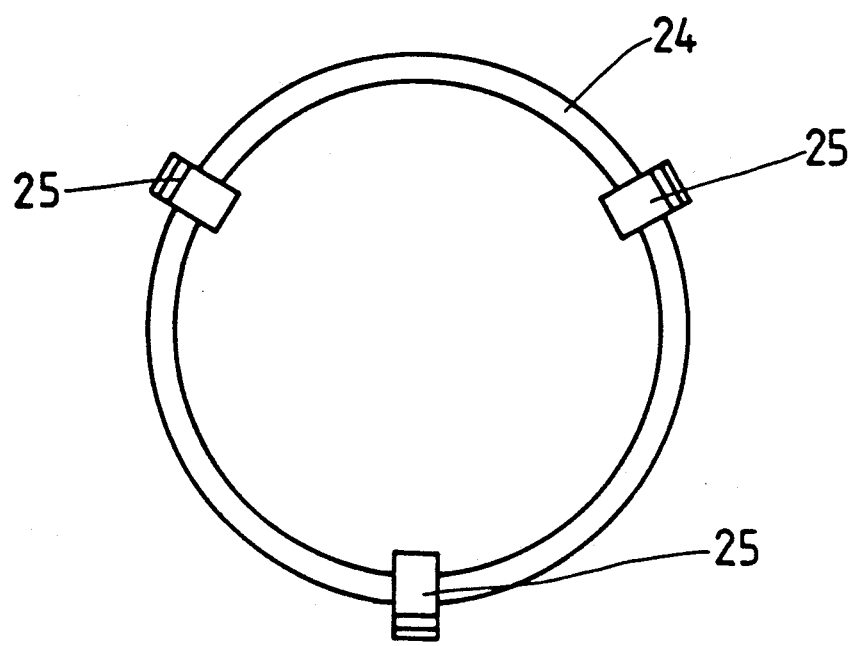

The base member may, as shown in FIG. 8, even be defined by a simple elastomeric band 24 carrying three claw units 25.

It will also be understood that numerous variations may be made to the above described embodiment of the invention without departing from the scope hereof which is limited simply to a fastener having a base member comprising at least three hook or tooth defining formations and whereof at least a part of the base member is elastically extensible in the general manner described above. In particular, the single shorter arm could be replaced by two or more spaced arms for engaging the portion of a diaper passing between the legs of a baby.

What I claim as new and desire to secure by Letters Patent is:

1. A safe diaper fastener for holding a fabric diaper on a baby comprising:
   an integral, flexible, elastically extensible plastic base member;
   three injection molded, unitary, relatively rigid plastic claw units; and
   three spaced apart attachment means on the base member for securing the claw units to edge portions of the base member;
   each of the claw units comprising:
   a flat body;

means on the flat body for engaging the attachment means and securing the claw unit to the base member;

means for engaging the fabric of the diaper without penetrating more than one layer of diaper fabric comprising a row of at least three teeth directed inwardly toward a central region of the body portion; and means for accommodating a gathering or bunching of diaper fabric beneath the flat body without disengaging the teeth from the fabric, comprising a transverse zone connecting the flat body and the teeth and spacing the teeth apart from the flat body.

2. A fastener as claimed in claim 1 wherein the claw units are separately manufactured and are substantially rigid units separably connected to the base member.

3. A fastener as claimed in claim 2 further comprising means for extending the elastically extensible part of the base member comprising an annular finger grip in proximity to each claw unit.

* * * * *